United States Patent
Noritake

(10) Patent No.: US 7,488,853 B2
(45) Date of Patent: Feb. 10, 2009

(54) PROCESS FOR PRODUCING PHENOLS

(75) Inventor: Tomoyuki Noritake, Chiba (JP)

(73) Assignee: Sumitomo Chemical Co., Ltd., Tokyo (JP)

( * ) Notice: Subject to any disclaimer, the term of this patent is extended or adjusted under 35 U.S.C. 154(b) by 0 days.

(21) Appl. No.: 11/675,279

(22) Filed: Feb. 15, 2007

(65) Prior Publication Data

US 2007/0197839 A1    Aug. 23, 2007

(30) Foreign Application Priority Data

Feb. 22, 2006  (JP) ............................. 2006-044991

(51) Int. Cl.
C07C 37/68 (2006.01)
(52) U.S. Cl. .................................... 568/754
(58) Field of Classification Search ............... 568/754
See application file for complete search history.

(56) References Cited

FOREIGN PATENT DOCUMENTS

| EP | 0 105 019 A2 | 4/1984 |
|---|---|---|
| JP | 2004-217538 A | 8/2004 |
| JP | 2005162710 A | * 6/2005 |

* cited by examiner

Primary Examiner—Daniel M Sullivan
Assistant Examiner—Kellette Gale
(74) Attorney, Agent, or Firm—Sughrue Mion, PLLC

(57) ABSTRACT

A process for producing a phenol, which comprises the following steps of:
- (1) oxidizing an alkylbenzene with an oxygen-containing gas to obtain an oxidation reaction mixture containing a hydroperoxide;
- (2) subjecting the oxidation reaction mixture to extraction operation with an alkaline aqueous solution to obtain an extract containing the hydroperoxide;
- (3) subjecting the extract obtained in the step (2) to extraction operation with an organic solvent to obtain an extract containing the hydroperoxide;
- (4) subjecting the extract obtained in the step (3) to water washing to obtain an oil layer containing the hydroperoxide, in which a content of the alkali has been reduced; and
- (5) subjecting the hydroperoxide contained in the oil layer obtained in the water washing step (4) to acidolysis to obtain a phenol, wherein a concentration of the hydroperoxide to be subjected to the water washing in the step (4), is 20% by weight or less.

3 Claims, No Drawings

PROCESS FOR PRODUCING PHENOLS

BACKGROUND OF THE INVENTION

1. Field of the Invention

The present invention relates to a process for producing a phenol. More particularly, the present invention relates to a process for producing a phenol, having an excellent effect that a separability of an oil layer and an aqueous layer in a washing step, can be heightened whereby the production of the phenol can be conducted under high productivity.

2. Description of the Related Art

There is disclosed in, for example, JP2005-162710 A, a process for producing a phenol by:

oxidizing a raw material containing an alkyl benzene with oxygen or air to obtain an oxidation reaction mixture containing a hydroperoxide;

extracting the oxidation reaction mixture with an alkali aqueous solution to obtain an extract (I) containing the hydroperoxide;

extracting the extract (I) with an organic solvent to obtain an extract (II) containing the hydroperoxide;

washing the extract (II) with water to separate into an oil layer containing the hydroperoxide, in which a content of the alkali is low, and an aqueous layer; and subjecting the hydroperoxide contained in the oil layer to acidolysis to obtain a phenol.

However, the above-described process did not have a good separability between the oil layer and the aqueous layer in the water washing step, therefore, it was insufficient from the viewpoint of realization of high productivity.

SUMMARY OF THE INVENTION

Under such situations, an object of the present invention is to provide a process for producing a phenol, having an excellent effect that a separability of an oil layer and an aqueous layer in a washing step, can be heightened whereby the production of the phenol can be conducted under high productivity.

Namely, the present invention relates to a process for producing a phenol, which comprises the following steps of:

(1) oxidizing an alkylbenzene with an oxygen-containing gas to obtain an oxidation reaction mixture containing a hydroperoxide;

(2) subjecting the oxidation reaction mixture to extraction operation with an alkaline aqueous solution to obtain an extract (herein-after, referred to as "extract-1") containing the hydroperoxide;

(3) subjecting the extract-1 to extraction operation with an organic solvent to obtain an extract (herein-after, referred to as "extract-2") containing the hydroperoxide;

(4) subjecting the extract-2 to water washing to obtain an oil layer containing the hydroperoxide, in which a content of the alkali has been reduced; and (5) subjecting the hydroperoxide contained in the oil layer obtained in the water washing step (4) to acidolysis to obtain a phenol, wherein a concentration of the hydroperoxide to be subjected to the water washing in the step (4), is 20% by weight or less.

DETAILED DESCRIPTION OF THE INVENTION

In the present invention, examples of the alkylbenzene include preferably mono- and di-$C_{1-10}$ alkylbenzenes (more preferably mono- and di-$C_{2-8}$ alkylbenzenes) such as ethylbenzene, m- and p-diethylbenzene, isopropylbenzene, m- or p-diisopropylbenzene, n-butylbenzene, m- or p-di-n-butylbenzene, t-butylbenzene, m- or p-di-t-butylbenzene, hexylbenzene, heptylbenzene and octylbenzene.

Further, in the present invention, examples of the phenol include preferably phenol, diphenols such as resorcinol and hydroquinone, and alkylphenols, more preferably phenol, resorcinol and hydroquinone.

As specific examples of the present invention, a case of which the alkylbenzene is m-diisopropylbenzene, the hydroperoxide is diisopropylbenzene dihydroperoxide and the phenol is resorcinol, is explained below, but the present invention is not restricted thereto in addition, the above-described case is representative one, and can be appropriately changed. Further, steps in the process described after, are also representative ones, therefore, it is possible to change appropriately, namely, to add a step, or delete or change the step within the scope of the present invention.

The oxidation step (1) is a step of obtaining the oxidation reaction mixture containing the hydroperoxide, by subjecting a raw material containing m-diisopropylbenzene to oxidation reaction with an oxygen-containing gas.

As the oxygen-containing gas, air, oxygen-enriched air or a dilute oxygen diluted with an inert gas such as nitrogen or argon, is used.

The raw material liquid for oxidation usually contains 20 to 60% by weight of m-diisopropylbenzene monohydroperoxide and 10 to 40% by weight of m-diisopropylbenzene. As usual reaction conditions, a temperature of 70 to 110° C., a pressure of 0 to 1 MPaG, a residence time of about 0.01 to 50 hours and the like are illustrated. As an apparatus used in the oxidation step, for example, a flowing type or batch type reaction vessel or reaction column can be listed. The oxidation reaction mixture obtained in the oxidation step usually contains 3 to 30% by weight of m-diisopropylbenzene dihydroperoxide and 20 to 60% by weight of m-diisopropylbenzene monohydroperoxide and 35% by weight or less of m-diisopropylbenzene.

The step (2) of extraction with an alkali in the present invention is a step of obtaining the extract-1 containing m-diisopropylbenzene dihydroperoxide by subjecting the oxidation reaction mixture to extraction operation with an alkali aqueous solution.

In the extraction step (2), a weight ratio of the alkali aqueous solution to the oxidation reaction mixture is usually 0.2 to 5. As the alkaline aqueous solution, a sodium hydroxide aqueous solution is preferable from the viewpoint of cost.

The alkali concentration of the alkaline aqueous solution is usually 0.1 to 30% by weight. As usual extraction conditions, a temperature of 0 to 70° C. and a countercurrent extraction of 1 to 10 stages are applied. As an apparatus used in extraction step (2) with an alkali aqueous solution, a mixer settler, extraction column or the like is listed.

The extraction step (3) with an organic solvent is a step of obtaining the extract-2 containing m-diisopropylbenzene dihydroperoxide by subjecting the extract-1 obtained in the extraction step (2) with an alkali aqueous solution to extract operation with an organic solvent.

The weight ratio of the extract-1 to the organic solvent is usually 0.2 to 10. Specific examples of the organic solvent include toluene, benzyl alcohol, cyclohexanol, pentanol, octanol, diisopropylketone, butanol, methylisopropylketone and methylisobutylketone. Usually, the extraction is usually 20 to 80° C. As an apparatus used in the extraction step (3) with the organic solvent, for example, a mixer settler or extraction column can be applied.

An alkali aqueous layer separated from the extract-1 in the extraction step (3) may be recycled to between an alkali extraction step (2) and an organic solvent extraction step (3).

The water washing step (4) is a step of obtaining an oil layer containing m-diisopropylbenzene dihydroperoxide, in which the alkali content has been reduced and an aqueous solution layer by subjecting the extract-2 obtained in the solvent extraction step (3) to water washing.

The weight ratio of the extract-2 to water is usually 0.1 to 10. A washing temperature is usually 20 to 80° C. As an apparatus used in the water washing step (4), for example, a mixer settler or extraction column can be applied.

The acidolysis step (5) is a step of obtaining resorcinol by subjecting m-diisopropylbenzene dihydroperoxide contained in the oil layer obtained in the water washing step (4) to acidolysis.

Examples of an acidic substance used in the acidolysis step (5), include sulfuric acid, sulfuric anhydride, fuming sulfuric acid, sulfur dioxide gas, benzene sulfonic acids such as p-toluene sulfonic acid and m-toluene sulfonic acid, methane sulfonic acid, trichloromethane sulfonic acid, trifluoromethane sulfonic acid, perchloric acid, phosphorous acid, polyphosphorous acid, hydrochloric acid, hydrofluoric acid, trichloroacetic acid, trifluoricacetic acid, aluminum chloride, trifluoro boron, a trifluoro boron complex (e.g. boron trifluoride-eterate), strong acidic ion exchange resins, perfluoric alkane sulfonic acids (e.g. perfluoromethane sulfonic acid), monochloroacetic acid, phosphorous tungstic acid, phosphorous molybdic acid, tin (IV) chloride, antimony chloride, sulfur tetrafluoride, silicon tetrafluoride, tungsten hexafluoride, tetrafluoroboron, hexafluorosilicic acid, hexafluorophosphorous acid and the like. Further, compounds containing sulfur and having a property of antioxidant can be also used. From the viewpoint of yield and easy handling, concentrated sulfuric acid, sulfuric anhydride or fuming sulfuric acid is preferable and sulfuric anhydride is more preferable.

Since preferable conditions for acidolysis change depending on the acidic material, those may be properly selected taking account of properties of the acidic material. For example, when sulfuric anhydride is used, the acidolysis is preferably conducted under conditions of a temperature of 50 to 150°°C., a molar ratio of the acidic material to hydroperoxy group of a hydroperoxy compound of about 0.0001 to 0.003 and a reaction time of about 0.1 to 15 minutes.

The greatest feature of the present invention is to control the concentration of the hydroperoxide contained in the extract-2 to be subjected to water washing to 20% by weight or less, preferably 15% by weight or less. When the concentration exceeds 20% by weight, a separability of an oil layer and an aqueous layer in the water washing step, deteriorates.

For maintaining the concentration of the hydroperoxide within the range of the present invention, for example, while monitoring the concentration of the hydroperoxide contained in the extract-2, the extraction conditions of the amount, temperature and the like of the solvent fed to the solvent extraction step, may be appropriately controlled. Further, the concentration of the hydroperoxide may be controlled by removing a part of the solvent through heating of the extract-2 or diluting with a solvent.

EXAMPLES

The present invention is explained by Examples in more detail below.

Examples 1 to 5 and Comparative Example 1

As a raw material, m-diisopropylbenzene containing about 40% by weight of m-diisopropylbenzene monohydroperoxide was subjected to continuous oxidation with air under conditions of a pressure of 0.3 MPaG, a temperature of 90° C. and a residence time of 10 hours to obtain an oxidation reaction mixture.

A 7 wt % sodium hydroxide aqueous solution was subjected to countercurrent contact with an oil layer (hereinafter, may be referred to as "oxidation oil") separated from the oxidation reaction mixture (a weight ratio of the sodium hydroxide aqueous solution to the oil layer was 0.7) at a temperature of about 40° C. to obtain an alkali aqueous solution containing hydroperoxides (Extract-1).

Thus obtained Extract-1 was contacted with methylisobutylketone (MIBK) of about 32° C. to obtain an alkali aqueous solution containing m-diisopropylbenzenedihydroperoxide, in which impurities were reduced. The alkali aqueous solution containing m-diisopropylbenzenedihydroperoxide was subjected to solvent extraction with MIBK in a weight ratio of MIBK as an organic solvent to the oxidation oil of 0.8 at about 61° C. to obtain an extract (Extract-2).

Thus obtained Extract-2 was used as it was, concentrated under a reduced pressure and a temperature of 90° C. by evaporating MIBK, or diluted with MIBK to prepare samples (MIBK solutions) having various hydroperoxide concentrations as shown in Table 1.

In water washing, each of samples was mixed with water in a volume ratio of the sample to water (sample/water) of 2 at ambient temperature, then the resulted mixture was allowed to stand still, and a period (separation time) for which the mixture after standing still separated into an oil layer and an aqueous layer, was measured. Results were shown in Table 1.

TABLE 1

|  | Hydroperoxide concentration (wt %) *1 | Separation time (Second) |
| --- | --- | --- |
| Example 1 | 10 | 120 |
| Example 2 | 12 | 220 |
| Example 3 | 13 | 240 |
| Example 4 | 15 | 390 |
| Example 5 | 6.5 | 30 |
| Comparative Example 1 | 22 | 4140 |

*1: Hydroperoxide was almost all m-diisopropylbenzenedihydroperoxide

According to the present invention, there can be provided a process for producing a phenol, having an excellent effect that a separability of an oil layer and an aqueous layer in a washing step, can be heightened whereby the production of the phenol can be conducted under high productivity.

The invention claimed is:

1. A process for producing a phenol, which comprises the following steps of:
   (1) oxidizing an alkylbenzene with an oxygen-containing gas to obtain an oxidation reaction mixture containing a hydroperoxide;
   (2) subjecting the oxidation reaction mixture to extraction operation with an alkaline aqueous solution to obtain an extract containing the hydroperoxide;
   (3) subjecting the extract obtained in the step (2) to extraction operation with an organic solvent to obtain an extract containing the hydroperoxide;
   (4) subjecting the extract obtained in the step (3) to water washing to obtain an oil layer containing the hydroperoxide, in which a content of the alkali has been reduced; and
   (5) subjecting the hydroperoxide contained in the oil layer obtained in the water washing step (4) to acidolysis to obtain a phenol,
   wherein a concentration of the hydroperoxide to be subjected to the water washing in the step (4), is 20% by weight or less.

2. The process according to claim 1, wherein the alkylbenzene is m-diisopropylbenzene.

3. A process for producing a phenol, which comprises the following steps of:

(1) oxidizing an alkylbenzene with an oxygen-containing gas to obtain an oxidation reaction mixture containing a hydroperoxide;

(2) subjecting the oxidation reaction mixture to extraction operation with an alkaline aqueous solution to obtain an extract containing the hydroperoxide;

(3) subjecting the extract obtained in the step (2) to extraction operation with an organic solvent to obtain an extract containing the hydroperoxide;

(4) subjecting the extract obtained in the step (3) to water washing to obtain an oil layer containing the hydroperoxide, in which a content of the alkali has been reduced; and (5) subjecting the hydroperoxide contained in the oil layer obtained in the water washing step (4) to acidolysis to obtain a phenol, wherein a concentration of the hydroperoxide to be subjected to the water washing in the step (4), is 15% by weight or less.

* * * * *